United States Patent
Irisawa et al.

(10) Patent No.: US 10,758,129 B2
(45) Date of Patent: Sep. 1, 2020

(54) PHOTOACOUSTIC IMAGE GENERATION APPARATUS AND INSERT

(71) Applicant: FUJIFILM Corporation, Tokyo (JP)

(72) Inventors: Kaku Irisawa, Kanagawa (JP); Tomoki Inoue, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 344 days.

(21) Appl. No.: 15/901,072

(22) Filed: Feb. 21, 2018

(65) Prior Publication Data

US 2018/0177408 A1 Jun. 28, 2018

Related U.S. Application Data

(63) Continuation of application No. PCT/JP2016/003796, filed on Aug. 22, 2016.

(30) Foreign Application Priority Data

Aug. 31, 2015 (JP) .................................. 2015-170512

(51) Int. Cl.
*A61B 5/00* (2006.01)
*A61B 8/00* (2006.01)
(Continued)

(52) U.S. Cl.
CPC ............ *A61B 5/0095* (2013.01); *A61B 5/061* (2013.01); *A61B 5/6848* (2013.01); *A61B 8/4254* (2013.01); *A61B 8/4416* (2013.01); *A61B 5/06* (2013.01); *A61B 8/08* (2013.01); *A61B 8/5261* (2013.01)

(58) Field of Classification Search
CPC ..... A61B 5/0095; A61B 5/061; A61B 5/6848; A61B 5/06; A61B 8/4254; A61B 8/4416; A61B 8/5261; A61B 8/08
See application file for complete search history.

(56) References Cited

U.S. PATENT DOCUMENTS

2004/0131299 A1 7/2004 Adoram et al.
2006/0241572 A1 10/2006 Zhou
(Continued)

FOREIGN PATENT DOCUMENTS

JP 2013-13713 A 1/2013
JP 2015-37519 A 2/2015
(Continued)

OTHER PUBLICATIONS

Extended European Search Report, dated Jul. 4, 2018, for European Application No. 16841076.9.
(Continued)

*Primary Examiner* — Peter Luong
(74) *Attorney, Agent, or Firm* — Birch, Stewart, Kolasch & Birch, LLP

(57) ABSTRACT

A puncture needle is at least partially inserted into a subject. An optical fiber guides light with a first wavelength and an optical fiber guides light with a second wavelength. The light guided by the optical fiber is emitted from a first light emitting portion and the light guided by the optical fiber is emitted from a second light emitting portion. A light absorption member absorbs the light with the first wavelength emitted from the first light emitting portion to generate photoacoustic waves and transmits the light with the second wavelength emitted from the second light emitting portion.

28 Claims, 9 Drawing Sheets

(51) Int. Cl.
*A61B 5/06* (2006.01)
*A61B 8/08* (2006.01)

(56) References Cited

U.S. PATENT DOCUMENTS

| | | |
|---|---|---|
| 2008/0108867 A1 | 5/2008 | Zhou |
| 2014/0180056 A1 | 6/2014 | Hoseit |
| 2015/0297092 A1 | 10/2015 | Irisawa |
| 2016/0135689 A1 | 5/2016 | Murakoshi |

FOREIGN PATENT DOCUMENTS

| | | |
|---|---|---|
| WO | WO 2014/109148 A1 | 7/2014 |
| WO | WO 2015/015932 A1 | 2/2015 |
| WO | WO 2015/111280 A1 | 7/2015 |

OTHER PUBLICATIONS

International Preliminary Report on Patentability and Written Opinion of the International Searching Authority (Forms PCT/IB/326, PCT/IB/373 and PCT/ISA/237) for Application No. PCT/JP2016/003796, dated Mar. 15, 2018, with an English translation.
International Search Report and English translation (Form PCT/ISA/210) for Application No. PCT/JP2016/003796, dated Nov. 29, 2016.

PHOTOACOUSTIC IMAGE GENERATION APPARATUS AND INSERT

CROSS-REFERENCE TO RELATED APPLICATIONS

This application is a continuation application of International Application No. PCT/JP2016/003796 filed Aug. 22, 2016, the disclosure of which is incorporated herein by reference in its entirety. Further, this application claims priority from Japanese Patent Application No. 2015-170512, filed Aug. 31, 2015, the disclosure of which is incorporated herein by reference in its entirety.

BACKGROUND OF THE INVENTION

1. Field of the Invention

The present invention relates to a photoacoustic image generation apparatus, and more particularly, to a photoacoustic image generation apparatus that detects photoacoustic waves generated by the absorption of light by a light absorber and generates a photoacoustic image.

In addition, the invention relates to an insert such as a puncture needle used in the photoacoustic image generation apparatus.

2. Description of the Related Art

An ultrasonography method has been known as a kind of image inspection method that can non-invasively inspect the internal state of a living body. In ultrasonography, an ultrasound probe that can transmit and receive ultrasonic waves is used. In a case in which the ultrasound probe transmits ultrasonic waves to a subject (living body), the ultrasonic waves travel in the living body and are reflected from the interface between tissues. The ultrasound probe receives the reflected ultrasonic waves and a distance is calculated on the basis of the time until the reflected ultrasonic waves return to the ultrasound probe. In this way, it is possible to capture an image indicating the internal aspect of the living body.

In addition, photoacoustic imaging has been known which captures the image of the inside of a living body using a photoacoustic effect. In general, in the photoacoustic imaging, the inside of the living body is irradiated with pulsed laser light. In the inside of the living body, a living body tissue absorbs the energy of the pulsed laser light and ultrasonic waves (photoacoustic waves) are generated by adiabatic expansion caused by the energy. For example, an ultrasound probe detects the photoacoustic waves and a photoacoustic image is formed on the basis of a detection signal. In this way, it is possible to visualize the inside of the living body on the basis of the photoacoustic waves.

For the photoacoustic imaging, JP2015-37519A discloses a technique in which light emitted from a light source is guided to the vicinity of a leading end of a puncture needle by, for example, an optical fiber and is emitted from the leading end to a photoacoustic wave generation portion of the puncture needle. The photoacoustic wave generation portion includes, for example, a light absorption member. JP2015-37519A discloses a technique in which the light absorption member can be made of, for example, an epoxy resin, a polyurethane resin, or a fluorine resin with which a black pigment is mixed, silicon rubber, or a black paint having high light absorbance with respect to the wavelength of laser light. In addition, JP2015-37519A discloses a technique in which a metal film or an oxide film having light absorptivity with respect to the wavelength of laser light is used as the light absorption member. An ultrasound probe detects the photoacoustic waves generated by the emission of light to the photoacoustic wave generation portion and a photoacoustic image is generated on the basis of a detection signal of the photoacoustic waves. In the photoacoustic image, a part of the photoacoustic wave generation portion appears as a bright point, which makes it possible to check the position of the puncture needle using the photoacoustic image.

Furthermore, JP2013-13713A discloses a puncture needle including a light emitting portion. In JP2013-13713A, light emitted from a light source is guided to the light emitting portion of the puncture needle by, for example, an optical fiber and is emitted from the light emitting portion to the outside. In a subject, photoacoustic waves are generated due to the absorption of the light emitted from the light emitting portion. An ultrasound probe detects the photoacoustic waves generated by the absorption of the light emitted from the light emitting portion of the puncture needle and a photoacoustic image is generated on the basis of the detection signal of the photoacoustic waves. In this way, it is possible to check the position of the puncture needle.

In JP2015-37519A, the light absorber provided at the leading end of the needle generates photoacoustic waves and the light absorber absorbs almost all of the light emitted to the photoacoustic wave generation portion. Therefore, even in a situation in which the light absorber is present in front of the needle in a needling direction in the subject, it is difficult for the light absorber to generate photoacoustic waves. For this reason, in JP2015-37519A, only the positional information of the tip of the needle can be acquired and it is difficult to acquire surrounding environment information such as information indicating whether the light absorber is present in the vicinity of the needle. In contrast, in JP2013-13713A, the light absorber that is present in front of the needle in the needling direction in the subject is irradiated with the light emitted from the light emitting portion. Therefore, in a case in which light with a wavelength absorbed by blood (blood vessel) is emitted from the light emitting portion, it is possible to determine whether the tip of the needle has been inserted into the blood vessel on the basis of whether a bright point is present in the photoacoustic image. However, in JP2013-13713A, the light emitting portion is exposed from, for example, a leading end portion of the needle and it is necessary to cover the leading end of the light emitting portion with an appropriate member.

In JP2013-13713A, the photoacoustic waves generated by the absorption of the light emitted from the light emitting portion by, for example, metal forming a puncture needle main body are detected in addition to the photoacoustic waves generated by the absorption of the light emitted from the light emitting portion by the light absorber that is present in front of the needle in the needling direction in the subject. However, it is considered that the intensity of the photoacoustic waves generated by the absorption of light by, for example, metal in JP2013-13713A is lower than the intensity of the photoacoustic waves generated by the absorption of light by the light absorber in JP2015-37519A. Therefore, it is considered that the positional information of the tip of the needle acquired in JP2013-13713A is not clearer than the positional information of the tip of the needle acquired in JP2015-37519A.

SUMMARY OF THE INVENTION

The invention has been made in view of the above-mentioned problems and an object of the invention is to provide a photoacoustic image generation apparatus that can acquire both positional information and surrounding environment information of an insert.

In addition, another object of the invention is to provide an insert that can acquire both the positional information and the surrounding environment information of the insert.

In order to achieve the objects, the invention provides an insert that is at least partially inserted into a subject. The insert includes: a first light guide member that guides light with a first wavelength; a first light emitting portion from which the light guided by the first light guide member is emitted; a second light guide member that guides light with a second wavelength different from the first wavelength; a second light emitting portion from which the light guided by the second light guide member is emitted; and a light absorption member that at least partially covers both the first light emitting portion and the second light emitting portion, absorbs the light with the first wavelength emitted from the first light emitting portion to generate photoacoustic waves, and transmits the light with the second wavelength emitted from the second light emitting portion.

In addition, the invention provides a photoacoustic image generation apparatus including: a first light source that emits light with a first wavelength; a second light source that emits light with a second wavelength different from the first wavelength; an insert that is at least partially inserted into a subject and includes a first light guide member which guides the light with the first wavelength, a first light emitting portion from which the light guided by the first light guide member is emitted, a second light guide member which guides the light with the second wavelength, a second light emitting portion from which the light guided by the second light guide member is emitted, and a light absorption member which at least partially covers both the first light emitting portion and the second light emitting portion, absorbs the light with the first wavelength emitted from the first light emitting portion to generate photoacoustic waves, and transmits the light with the second wavelength emitted from the second light emitting portion; acoustic wave detection unit for detecting first photoacoustic waves which are generated by the absorption of the light with the first wavelength by the light absorption member and second photoacoustic waves which are generated in the subject due to the light emitted from the second light emitting portion; and photoacoustic image generation unit for generating a first photoacoustic image on the basis of the first photoacoustic waves, generating a second photoacoustic image on the basis of the second photoacoustic waves, and generating a third photoacoustic image on the basis of both the first photoacoustic waves and the second photoacoustic waves.

DESCRIPTION OF THE PREFERRED EMBODIMENTS

Figure 1:
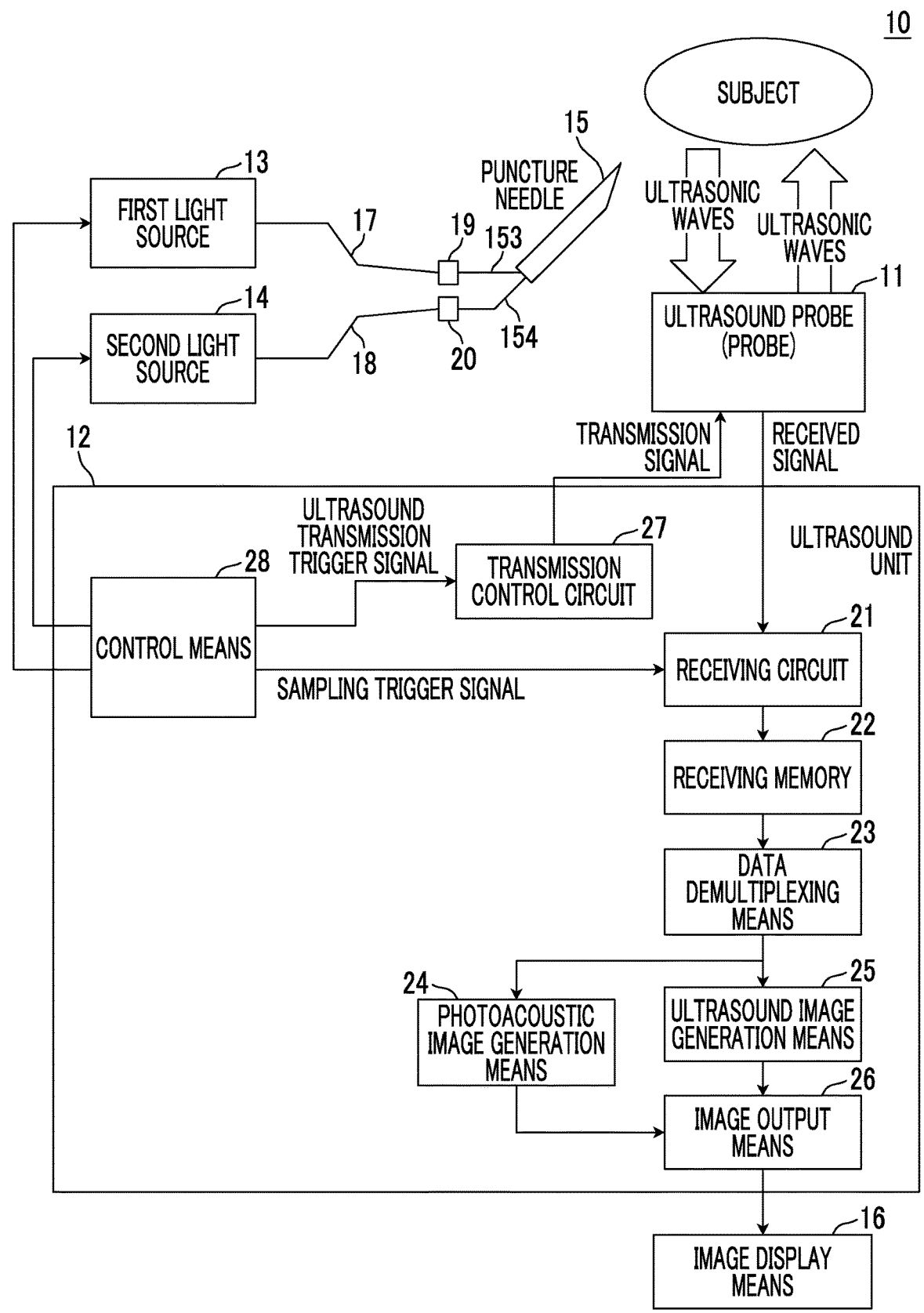
FIG. 1 is a block diagram illustrating a photoacoustic image generation apparatus according to a first embodiment of the invention.

Hereinafter, embodiments of the invention will be described in detail with reference to the drawings. FIG. 1 illustrates a photoacoustic image generation apparatus according to a first embodiment of the invention. A photoacoustic image generation apparatus 10 includes a probe (ultrasound probe) 11, an ultrasound unit 12, a first light source (laser unit) 13, a second light source (laser unit) 14, and a puncture needle 15. In the embodiment of the invention, ultrasonic waves are used as acoustic waves. However, the invention is not limited to the ultrasonic waves. Acoustic waves with an audible frequency may be used as long as an appropriate frequency can be selected according to, for example, an inspection target or measurement conditions.

The first light source 13 emits light with a first wavelength. The second light source 14 emits light with a second wavelength. For example, the first light source 13 and the second light source 14 emit pulsed light with a pulse energy of about 0.3 µJ to 30 µJ and a pulse time width of about 1 ns to 100 ns. The first wavelength and the second wavelength are different from each other. The first light source 13 and the second light source 14 are, for example, solid-state laser light sources. The type of light source is not particularly limited. The first light source 13 and the second light source 14 may be laser diode light sources (semiconductor laser light sources) or light amplifying laser light sources having a laser diode light source as a seed light source. In addition, light sources other than the laser light source may be used.

The light with the first wavelength emitted from the first light source 13 is guided to the puncture needle 15 by light guide means, such as an optical fiber 17, and a light guide member (first light guide member), such as an optical fiber 153. The light with the second wavelength emitted from the second light source 14 is guided to the puncture needle 15 by light guide means, such as an optical fiber 18, and a light guide member (second light guide member), such as an optical fiber 154.

The puncture needle 15 is a needle that is inserted into a subject. The optical fiber 153 and the optical fiber 154 are inserted into the puncture needle 15. An optical connector 19 is provided between the optical fiber 17 close to the first light source 13 and the optical fiber 153 inserted into the puncture needle 15. The optical connector 19 detachably connects the optical fiber 17 and the optical fiber 153. Similarly, an optical connector 20 is provided between the optical fiber 18 close to the second light source 14 and the optical fiber 154 inserted into the puncture needle 15. The optical connector 20 detachably connects the optical fiber 18 and the optical fiber 154. The connection of the optical connector 19 and the optical connector 20 is released to throw away the optical fiber 153 and optical fiber 154 together with the puncture needle 15 at the same time.

Figure 2:
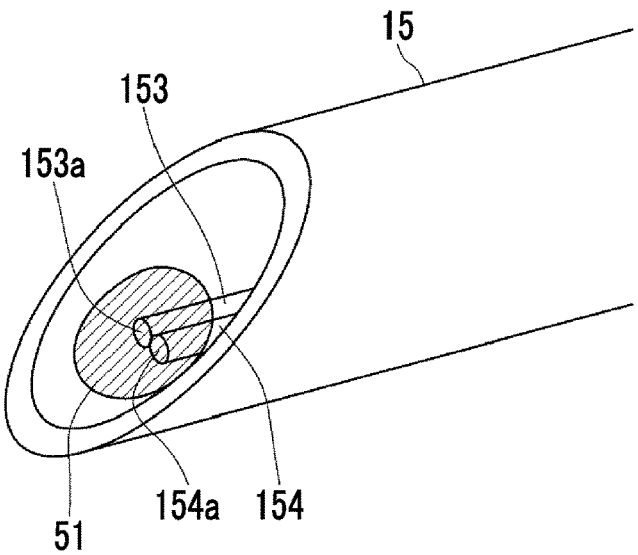
FIG. 2 is a perspective view illustrating the vicinity of a leading end of a puncture needle.

FIG. 2 illustrates the vicinity of a leading end of the puncture needle 15. The puncture needle 15 has a light absorption member 51 provided in the vicinity of the leading end. A leading end (a far end as viewed from the light source side) of the optical fiber 153 forms a light emitting portion (first light emitting portion) 153a from which guided light is emitted. A leading end of the optical fiber 154 forms a light emitting portion (second light emitting portion) 154a from which guided light is emitted. For example, the light absorption member 51 at least partially covers the first light emitting portion 153a and the second light emitting portion 154a. The light absorption member 51 may also function as a fixing member that fixes the optical fiber 153 and the optical fiber 154 to the inner wall of an inner cavity of the puncture needle 15. The optical fiber 153 and the optical fiber 154 may be coated. For example, polyimide, a fluorine resin, or an acrylic resin may be used for coating.

The light absorption member 51 absorbs the light with the first wavelength emitted from the first light emitting portion 153a and generates photoacoustic waves. The light absorption member 51 is provided in the vicinity of the leading end of the puncture needle 15 and can generate photoacoustic waves at a point in the vicinity of the leading end of the puncture needle 15. Since the length of a generation source (sound source) of the photoacoustic waves is sufficiently smaller than the total length of the puncture needle, the sound source can be regarded as a point sound source. In addition, the light absorption member 51 does not absorb the light with the second wavelength emitted from the second light emitting portion 154a and transmits the light with the second wavelength to the outside of an opening portion provided at the leading end of the puncture needle 15. Even in a case in which the light with the second wavelength is emitted from the second light emitting portion 154a, the light absorption member 51 does not generate photoacoustic waves since the light absorption member 51 does not absorb the light with the second wavelength.

The first light emitting portion 153a is provided in the vicinity of the leading end of the puncture needle 15. The optical fiber 153 guides the light with the first wavelength which is incident from the first light source 13 to the vicinity of the leading end of the puncture needle 15. The second light emitting portion 154a is also provided in the vicinity of the leading end of the puncture needle 15 and the optical fiber 154 guides the light with the second wavelength which is incident from the second light source 14 to the vicinity of the leading end of the puncture needle 15. Here, "the vicinity of the leading end" means a position where the light absorption member 51 provided at the leading end can generate photoacoustic waves capable of imaging the position of the leading end of the puncture needle 15 with accuracy required for a needling operation in a case in which the light emitting portion 153a and the light emitting portion 154a are disposed at the position. For example, the vicinity of the leading end is the range of 0 mm to 3 mm from the leading end to the base end of the puncture needle 15.

In a case in which the light absorption member 51 transmits the light with the second wavelength, the light absorption member 51 does not need to transmit all of the light with the second wavelength. That is, the light absorbance of the light absorption member 51 does not need to be 0%. The light absorption member 51 may absorb and transmit the light with the second wavelength at a ratio of, for example, about 1:9. Similarly, in a case in which the light absorption member 51 absorbs the light with the first wavelength, the light absorption member 51 does not need to absorb all of the light with the first wavelength. That is, the light absorbance of the light absorption member 51 does not need to be 100%. The light absorption member 51 may absorb and transmit the light with the first wavelength at a ratio of, for example, about 9:1. The same description holds for the transmission of the light with the second wavelength and the absorption of the light with the first wavelength or light with a third wavelength which will be described below.

The light absorption member 51 includes, for example, a light absorber that absorbs the light with the first wavelength and transmits the light with the second wavelength and a resin (for example, an epoxy resin) including the light absorber. For example, in a case in which a pulsed laser diode with a wavelength of 905 nm is used as the first light source 13, a material that absorbs light with the wavelength is mixed as the light absorber with a resin. For example, the following material can be used as the light absorber: YKR-2900 or YKR-2081 which is a phthalocyanine-based material manufactured by Yamamoto Chemical Industry Co., Ltd.; FDN-004 or FDN-005 manufactured by Yamada Chemical Co., Ltd.; a cyanine-based absorber material disclosed in JP5243056B; IRA908, IRA912, or IRA931 manufactured by Exciton Inc.; or S0433 manufactured by FEW Chemicals GmbH. In a case in which these absorbers are used, a pulsed laser diode with a wavelength of 870 nm may be used as the first light source 13.

In a case in which a resin including the above-mentioned absorber is used as the light absorption member 51, light with a wavelength of 905 nm emitted from the first light source 13 is converted into acoustic waves. The acoustic waves can be used to detect the position of the leading end of the puncture needle 15. In contrast, light emitted from the second light source 14 is transmitted through the light absorption member 51 and is emitted to the outside of the puncture needle 15. The light can be used to evaluate the surrounding environment of the leading end portion of the puncture needle 15. The wavelength of the light emitted from the second light source 14 can be appropriately selected from a wavelength range in which absorbance is high in the absorbance-wavelength characteristics of the absorber.

Figure 3:
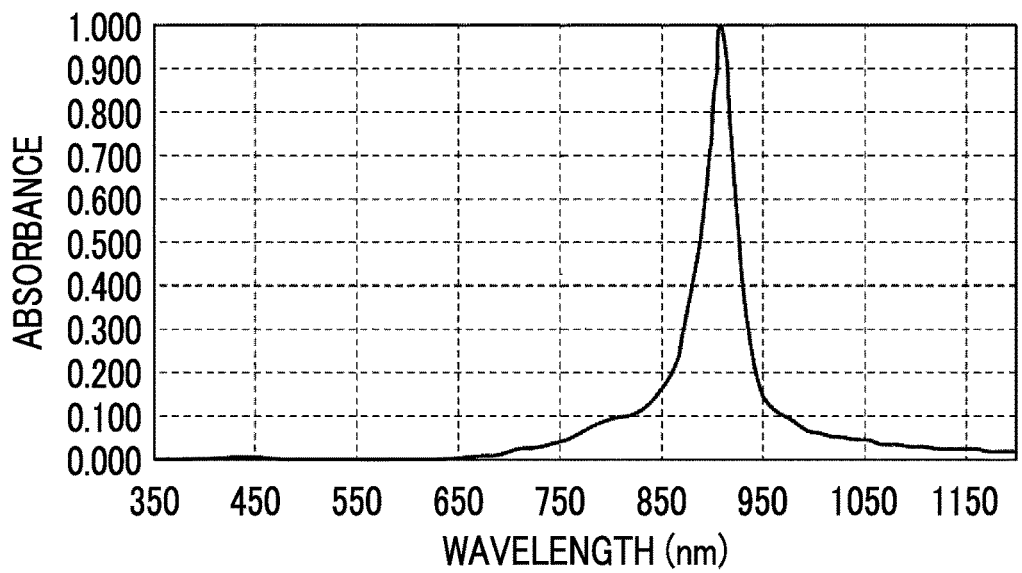
FIG. 3 is a graph illustrating an example of an absorption spectrum of a light absorption member.

FIG. 3 illustrates an example of the absorption spectrum of the light absorption member 51. The horizontal axis indicates a wavelength and the vertical axis indicates absorbance. A cyanine-based absorber material is used as the absorber included in the light absorption member 51. In the light absorption member 51, the absorbance of light with a wavelength of about 905 nm is the highest and the absorbance of light is rapidly reduced toward a long wavelength side and a short wavelength side. In a case in which the light absorption member 51 is used, the wavelength of the light emitted from the second light source 14 may be appropriately selected from the range of 400 nm to 650 nm or the range of 1000 nm or more.

The second wavelength is set according to materials around the part into which the puncture needle 15 is inserted. In other words, the second wavelength is set according to an evaluation target material in the surrounding environment of the puncture needle 15. A light source emitting light with a wavelength which is absorbed by an evaluation target material to generate photoacoustic waves is used as the second light source. For example, in a case in which the evaluation target is blood (blood vessel), a light source that emits light with a wavelength of 530 nm is used as the second light source 14. In a case in which the evaluation target is a nerve, a light source that emits light with a wavelength of 1210 nm is used as the second light source 14.

In a case in which the evaluation target is a contrast agent used to visualize, for example, a lymph node or a lymph tube, a light source emitting light with a wavelength which is absorbed by the contrast agent to generate photoacoustic waves may be used as the second light source 14. For example, in a case in which indocyanine green (ICG) is used as the contrast agent, a light source that emits light with a wavelength of 780 nm may be used as the second light source 14. In a case in which methylene blue is used as the contrast agent, a light source that emits light with a wavelength of 663 nm may be used. In a case in which Patent Blue V is used as the contrast agent, a light source that emits light with a wavelength of 638 nm may be used.

In a case in which a specific material is transferred to, for example, a cancer cell by a drug delivery system (DDS) and it is evaluated whether the material is present, a light source emitting light with a wavelength which is absorbed by the material to generate photoacoustic waves may be used as the second light source 14. For example, in a case in which the evaluation target is a gold nanoparticle, a light source that emits light in the wavelength range of 600 nm to 900 nm according to the diameter of the gold nanoparticle may be used as the second light source 14. In a case in which the evaluation target is a carbon nanotube, a light source that emits light in the wavelength range of 670 nm to 820 nm may be used as the second light source 14.

The first light source 13 is not limited to the light source that emits only the light with the first wavelength. A light source that can emit light components with a plurality of wavelengths may be used as the first light source 13 and may emit light components with wavelengths different from the light with the first wavelength. An example of the light source that can emit light components with a plurality of wavelengths including the first wavelength (905 nm) is a Ti:Sf laser or a Nd:YAG-optical parametric oscillation (OPO) laser.

In addition, the second light source 14 is not limited to the light source that emits only the light with the second wavelength. The second light source 14 does not need to be only one light source and the second light source 14 may have two or more light sources. In this case, for example, a wavelength division multiplexing coupler that multiplexes light components with a plurality of wavelengths emitted from a plurality of light sources may be provided on an optical path through which light emitted from the second light source 14 is incident on the optical fiber 154. For example, the photoacoustic image generation apparatus 10 may include, as the second light source 14, a light source that emits light with a wavelength of 530 nm and a light source that emits light with a wavelength of 1210 nm. In this case, the user may select which of the light sources in the second light source 14 is to be used to emit light according to the evaluation target. Specifically, in a case in which the evaluation target is blood (blood vessel), a light source that emits light with a wavelength of 530 nm may be selected to emit light. In a case in which the evaluation target is a nerve, a light source that emits light with a wavelength of 1210 nm may be selected to emit light. For example, a menu for selecting an evaluation target may be provided on a menu screen such that the user can select the light source to be used to emit light.

In a case in which the second light source 14 includes two or more light sources, two or more light sources may be controlled such that they emit light in time series while being switched. In this case, each light source may emit light, photoacoustic waves (second photoacoustic waves) may be detected, and second photoacoustic images corresponding to light components with each wavelength may be generated. In this case, the second photoacoustic images corresponding to light components with each wavelength are displayed while being switched or are displayed side by side such that a plurality of types of evaluation targets can be evaluated.

The second light source 14 does not necessarily include light sources that emit light with a plurality of single wavelengths and may be a light source that can emit light components with a plurality of wavelengths while switching the light components. For example, OPO may be used for the second light source 14. The OPO may be performed in a broad band and light with an arbitrary wavelength may be dispersed in the broad band to select a wavelength. In addition, the second light source 14 may emit light components with a plurality of wavelengths different from the first wavelength while switching the light components and photoacoustic waves corresponding to the light components may be detected. Then, the relationship between the wavelength and the intensity of the detected photoacoustic waves may be calculated to evaluate a surrounding environment. The surrounding environment may be evaluated to evaluate melanin (metastatic malignant melanoma), to monitor a cauterized state, to monitor tissue death caused by ethanol infusion, to detect nerve peaks, to evaluate the behavior of artheroma plaque, to evaluate liver fibrosis (scattering), and to evaluate the degree of progress of inflammation.

Figure 4:
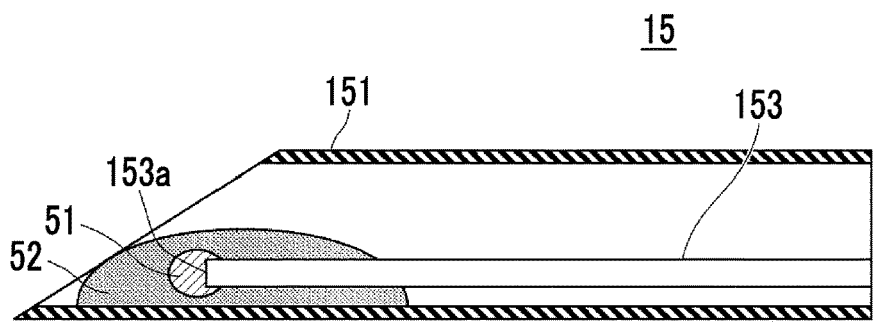
FIG. 4 is a cross-sectional view illustrating the vicinity of a leading end of a puncture needle according to a modification example.

The puncture needle 15 may further include a transparent resin that transmits at least the light with the second wavelength. FIG. 4 is a cross-sectional view illustrating the leading end portion of the puncture needle 15 including the transparent resin. In FIG. 4, the optical fiber 154 which is a second light guide member is not illustrated. A transparent resin 52 transmits at least the light with the second wavelength. The transparent resin 52 may transmit most of incident light with the second wavelength and does not need to transmit all of the incident light with the second wavelength. That is, the transparent resin 52 does not need to transmit 100% of the light with the second wavelength. For example, an epoxy resin (adhesive) is used as the transparent resin 52. For example, a thermosetting resin, an ultraviolet-curable resin, or a photocurable resin is used as the transparent resin 52.

A puncture needle main body 151 forming a main body portion of the puncture needle 15 has an inner cavity. The transparent resin 52 covers the light absorption member 51 in the inner cavity of the puncture needle main body 151. The transparent resin 52 may cover at least one of the optical fiber 153 or the optical fiber 154 (not illustrated) in the inner cavity of the puncture needle main body 151. The transparent resin 52 may function as a fixing member that fixes the light absorption member 51, the optical fiber 153, and the optical fiber 154 to the inner wall of the puncture needle main body 151. In FIG. 4, the light absorption member 51 covers the light emitting portion 153a of the optical fiber 153 and (the leading end portion of) the optical fiber 153 and the light absorption member 51 are fixed to the inner wall of the puncture needle main body 151 by the transparent resin 52.

The light absorption member 51 also covers the light emitting portion 154a of the optical fiber 154 (not illustrated) and the optical fiber 154 is also fixed to the inner wall of the puncture needle main body 151 by the transparent resin 52.

Returning to FIG. 1, the probe 11 includes, for example, a plurality of detector elements (ultrasound transducers) which are acoustic wave detection means and are one-dimensionally arranged. After the puncture needle 15 is inserted into the subject, the probe 11 detects the photoacoustic waves (first photoacoustic waves) generated from the light absorption member 51 (see FIG. 2) and photoacoustic waves (second photoacoustic waves) generated in the subject due to light emitted from the second light emitting portion 154a (see FIG. 2). The probe 11 performs the transmission of acoustic waves (ultrasonic waves) to the subject and the reception of the reflected acoustic waves (reflected ultrasonic waves) with respect to the transmitted ultrasonic waves, in addition to the detection of the photoacoustic waves. The transmission and reception of the sound waves may be performed at different positions. For example, ultrasonic waves may be transmitted from a position different from the position of the probe 11 and the probe 11 may receive the reflected ultrasonic waves with respect to the transmitted ultrasonic waves. The probe 11 is not limited to a linear probe and may be a convex probe or a sector probe.

The ultrasound unit 12 includes a receiving circuit 21, a receiving memory 22, data demultiplexing means 23, photoacoustic image generation means 24, ultrasound image generation means 25, image output means 26, a transmission control circuit 27, and control means 28. The ultrasound unit 12 forms a signal processing device. The ultrasound unit 12 typically includes a processor, a memory, and a bus. A program related to the generation of a photoacoustic image is incorporated into the ultrasound unit 12. The program is executed to implement the functions of at least some of the components in the ultrasound unit 12.

The receiving circuit 21 receives a detection signal output from the probe 11 and stores the received detection signal in the receiving memory 22. The receiving circuit 21 typically includes a low noise amplifier, a variable gain amplifier, a low-pass filter, and an analog-to-digital convertor (AD convertor). The detection signal from the probe 11 is amplified by the low noise amplifier. The gain of the detection signal is adjusted by the variable gain amplifier according to a depth and a high-frequency component of the detection signal is cut by the low-pass filter. Then, the detection signal is converted into a digital signal by the AD convertor and is stored in the receiving memory 22. The receiving circuit 21 includes, for example, one integrated circuit (IC).

The probe 11 outputs a detection signal of the photoacoustic waves and a detection signal of the reflected ultrasonic waves. The AD-converted detection signals (sampling data) of the photoacoustic waves and the reflected ultrasonic waves are stored in the receiving memory 22. The data demultiplexing means 23 reads out the sampling data of the detection signal of the photoacoustic waves from the receiving memory 22 and transmits the sampling data to the photoacoustic image generation means 24. In addition, the data demultiplexing means 23 reads out the sampling data of the reflected ultrasonic waves from the receiving memory 22 and transmits the sampling data to the ultrasound image generation means (reflected acoustic image generation means) 25.

The photoacoustic image generation means 24 generates a photoacoustic image on the basis of the detection signal of the photoacoustic waves detected by the probe 11. The generation of the photoacoustic image includes, for example, image reconfiguration, such as phasing addition, detection, and logarithmic conversion. The ultrasound image generation means 25 generates an ultrasound image (reflected acoustic image) on the basis of the detection signal of the reflected ultrasonic waves detected by the probe 11. The generation of the ultrasound image includes, for example, image reconfiguration, such as phasing addition, detection, and logarithmic conversion. The image output means 26 outputs the photoacoustic image and the ultrasound image to image display means 16 such as a display device.

The control means 28 controls each component in the ultrasound unit 12. For example, in a case in which a photoacoustic image is acquired, the control means 28 transmits a trigger signal to the first light source 13 or the second light source 14 such that the first light source 13 or the second light source 14 emits laser light. In addition, the control means 28 transmits a sampling trigger signal to the receiving circuit 21 to control, for example, the sampling start time of the photoacoustic waves with the emission of the laser light.

In a case in which an ultrasound image is acquired, the control means 28 transmits an ultrasound transmission trigger signal for instructing the transmission of ultrasonic waves to the transmission control circuit 27. In a case in which the ultrasound transmission trigger signal is received, the transmission control circuit 27 directs the probe 11 to transmit ultrasonic waves. For example, the probe 11 performs scanning while shifting acoustic lines one by one to detect reflected ultrasonic waves. The control means 28 transmits a sampling trigger signal to the receiving circuit 21 in synchronization with the transmission of the ultrasonic waves to start the sampling of the reflected ultrasonic waves.

The control means 28 may switch the operation mode of the photoacoustic image generation apparatus 10 among four operation modes. In a first operation mode, the first light source 13 emits light with the first wavelength, the photoacoustic waves (first photoacoustic waves) generated from the light absorption member 51 are detected, and a photoacoustic image (first photoacoustic image) is generated. In a second operation mode, the second light source 14 emits light with the second wavelength, the photoacoustic waves (second photoacoustic waves) generated by the irradiation of the subject with the light with the second wavelength transmitted through the light absorption member 51 are detected, and a photoacoustic image (second photoacoustic image) is generated. In a third operation mode, the first light source 13 emits light with the first wavelength, the second light source 14 emits light with the second wavelength, both the photoacoustic waves (first photoacoustic waves) generated from the light absorption member 51 and the photoacoustic waves (second photoacoustic waves) generated by the irradiation of the subject with the light with the second wavelength transmitted through the light absorption member 51 are detected, and a photoacoustic image (third photoacoustic image) is generated. In a fourth operation mode, ultrasonic waves are transmitted to the subject, ultrasonic waves reflected from the subject are detected, and an ultrasound image is generated. A user, such as a doctor, can select the operation mode using input means (not illustrated), such as a keyboard or a console switch. Alternatively, arbitrary operation modes among the four operation modes may be sequentially automatically switched and images obtained in each operation mode may be combined and displayed.

Figure 5:
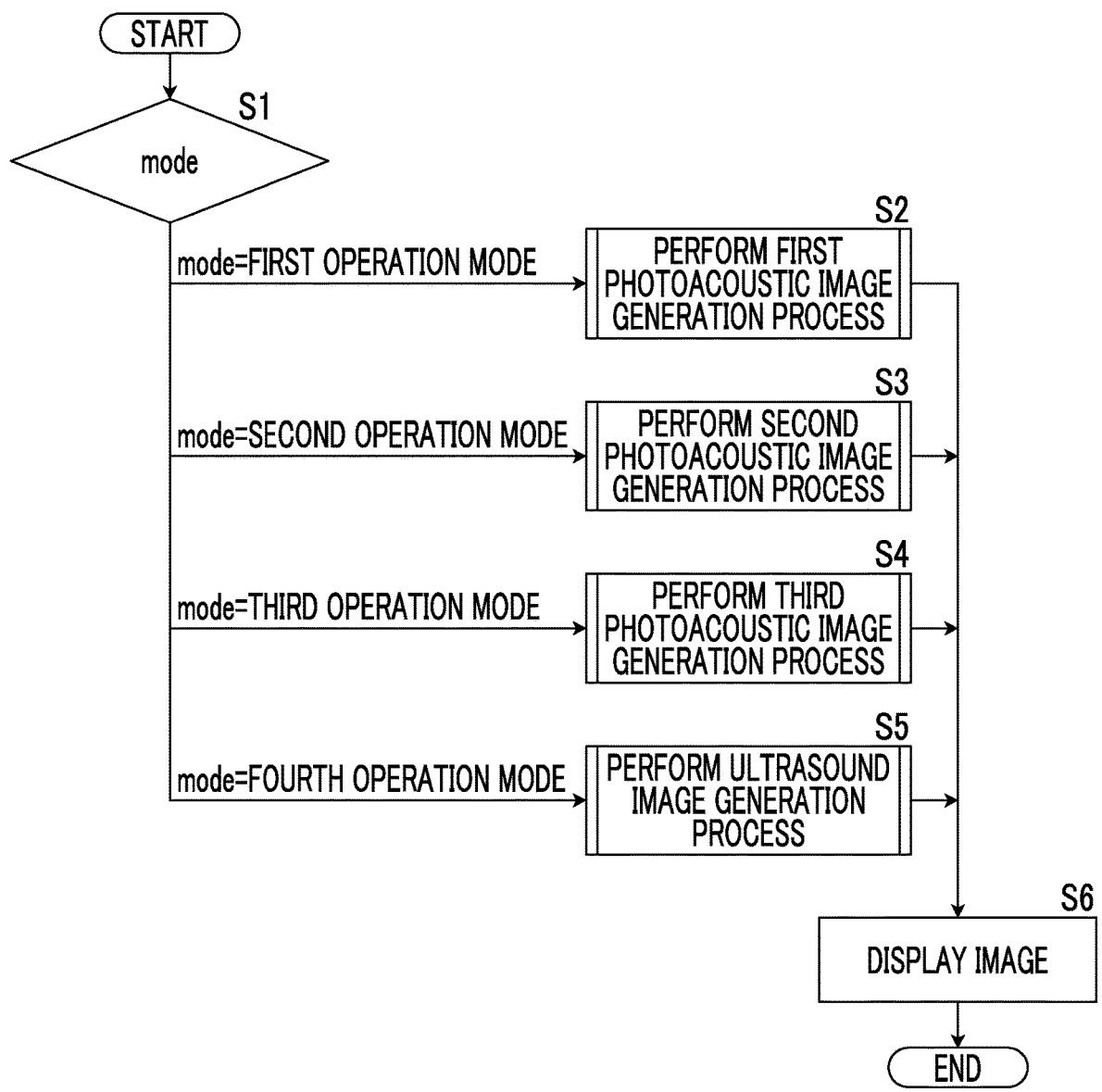
FIG. 5 is a flowchart illustrating the procedure of an operation of the photoacoustic image generation apparatus.

Next, the procedure of an operation will be described. FIG. 5 illustrates the procedure of the operation of the photoacoustic image generation apparatus 10. The operation mode selected by the user is stored in a variable mode. The control means 28 switches a process according to the variable mode (Step S1). In a case in which the variable mode is the first operation mode, the control means 28 performs a first photoacoustic image generation process in the photoacoustic image generation apparatus 10 (Step S2). In a case in which the variable mode is the second operation mode, the control means 28 performs a second photoacoustic image generation process in the photoacoustic image generation apparatus 10 (Step S3). In a case in which the variable mode is the third operation mode, the control means 28 performs a third photoacoustic image generation process in the photoacoustic image generation apparatus 10 (Step S4). In a case in which the variable mode is the fourth operation mode, the control means 28 performs an ultrasound image generation process in the photoacoustic image generation apparatus 10 (Step S5). The photoacoustic image generation apparatus 10 displays the image generated in Step S2, Step S3, Step S4, or Step S5 on the image display means 16 (Step S6).

Figure 6:
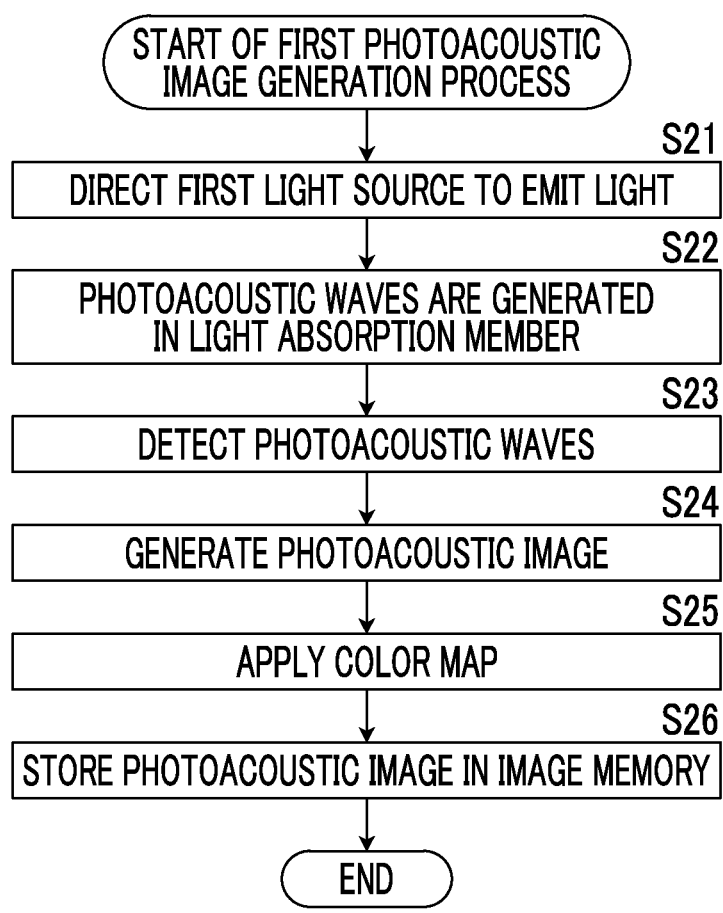
FIG. 6 is a flowchart illustrating the procedure of a first photoacoustic image generation process.

FIG. 6 illustrates the procedure of the first photoacoustic image generation process. The control means 28 directs the first light source 13 to emit light (Step S21). In Step S21, the control means 28 transmits a trigger signal to the first light source 13. In a case in which the first light source 13 is a solid-state laser device including a flash lamp and a Q-switch, the trigger signal includes, for example, a flash lamp trigger signal and a Q-switch trigger signal. In the first light source 13, the flash lamp is turned on in response to the flash lamp trigger signal and then the Q-switch is driven in response to the Q-switch trigger signal to emit pulsed laser light with the first wavelength. In a case in which the first light source 13 is a laser diode, a laser driver circuit makes a predetermined amount of current flow to the laser diode for the time corresponding to a pulse width in response to the trigger signal to emit pulsed laser light with the first wavelength.

The pulsed laser light emitted from the first light source 13 is incident on the optical fiber 153 through the optical fiber 17 and the optical connector 19, is guided to the vicinity of the leading end of the puncture needle 15 by the optical fiber 153, and is emitted from the first light emitting portion 153a (see FIG. 2). At least a portion of the pulsed laser light is emitted to the light absorption member 51 provided at the leading end of the puncture needle 15. The light absorption member 51 absorbs the light with the first wavelength and generates photoacoustic waves (Step S22).

The probe 11 detects the photoacoustic waves generated by the emission of the laser light, that is, the photoacoustic waves (first photoacoustic waves) generated from the light absorption member 51 (Step S23). The photoacoustic waves detected by the probe are received by the receiving circuit 21 and the sampling data of the photoacoustic waves is stored in the receiving memory 22. The photoacoustic image generation means 24 receives the sampling data of the detection signal of the photoacoustic waves through the data demultiplexing means 23 and generates a photoacoustic image (first photoacoustic image) (Step S24). The photoacoustic image generation means 24 may apply a color map (Step S25) to convert the signal intensity of the photoacoustic image into a color. The photoacoustic image generated by the photoacoustic image generation means 24 is stored in, for example, an image memory (not illustrated) of the image output means 26 (Step S26).

Figure 7:
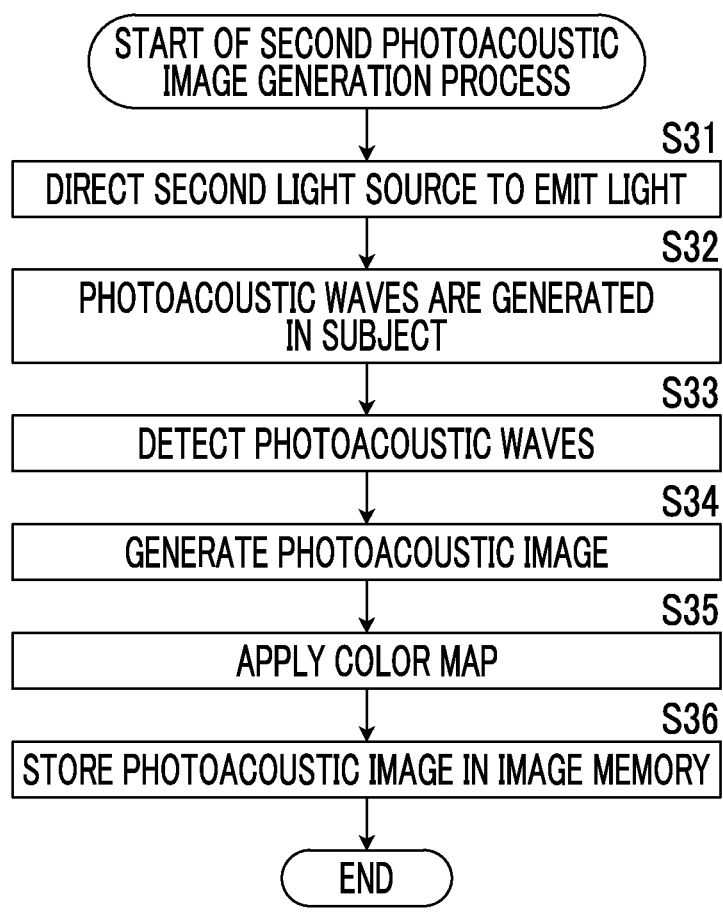
FIG. 7 is a flowchart illustrating the procedure of a second photoacoustic image generation process.

FIG. 7 illustrates the procedure of the second photoacoustic image generation process. The control means 28 directs the second light source 14 to emit light (Step S31). In Step S31, the control means 28 transmits a trigger signal to the second light source 14. In a case in which the second light source 14 is a solid-state laser device including a flash lamp and a Q-switch, the trigger signal includes, for example, a flash lamp trigger signal and a Q-switch trigger signal. In the second light source 14, the flash lamp is turned on in response to the flash lamp trigger signal and then the Q-switch is driven in response to the Q-switch trigger signal to emit pulsed laser light with the second wavelength. In a case in which the second light source 14 is a laser diode, a laser driver circuit makes a predetermined amount of current flow to the laser diode for the time corresponding to a pulse width in response to the trigger signal to emit pulsed laser light with the first wavelength.

The pulsed laser light emitted from the second light source 14 is incident on the optical fiber 154 through the optical fiber 18 and the optical connector 20, is guided to the vicinity of the leading end of the puncture needle 15 by the optical fiber 154, and is emitted from the second light emitting portion 154a (see FIG. 2). Since the light absorption member 51 covering the second light emitting portion 154a transmits light with the second wavelength, the pulsed laser light with the second wavelength emitted from the second light emitting portion 154a is emitted from the opening of the puncture needle 15 into the subject. In a case in which an absorber that absorbs light with the second wavelength is present in the emission range of the pulsed laser light with the second wavelength, photoacoustic waves (second photoacoustic waves) are generated from the absorber (Step S32).

The probe 11 detects the photoacoustic waves generated by the emission of the laser light, that is, the photoacoustic waves (second photoacoustic waves) generated from the subject (Step S33). The photoacoustic waves detected by the probe are received by the receiving circuit 21 and the sampling data of the photoacoustic waves is stored in the receiving memory 22. The photoacoustic image generation means 24 receives the sampling data of the detection signal of the photoacoustic waves through the data demultiplexing means 23 and generates a photoacoustic image (second photoacoustic image) (Step S34). The photoacoustic image generation means 24 may apply a color map (Step S35) to convert the signal intensity of the photoacoustic image into a color. It is preferable that the color map used in Step S35 is different from the color map used to generate the first photoacoustic image. The photoacoustic image generated by the photoacoustic image generation means 24 is stored in, for example, the image memory (not illustrated) of the image output means 26 (Step S36).

Figure 8:
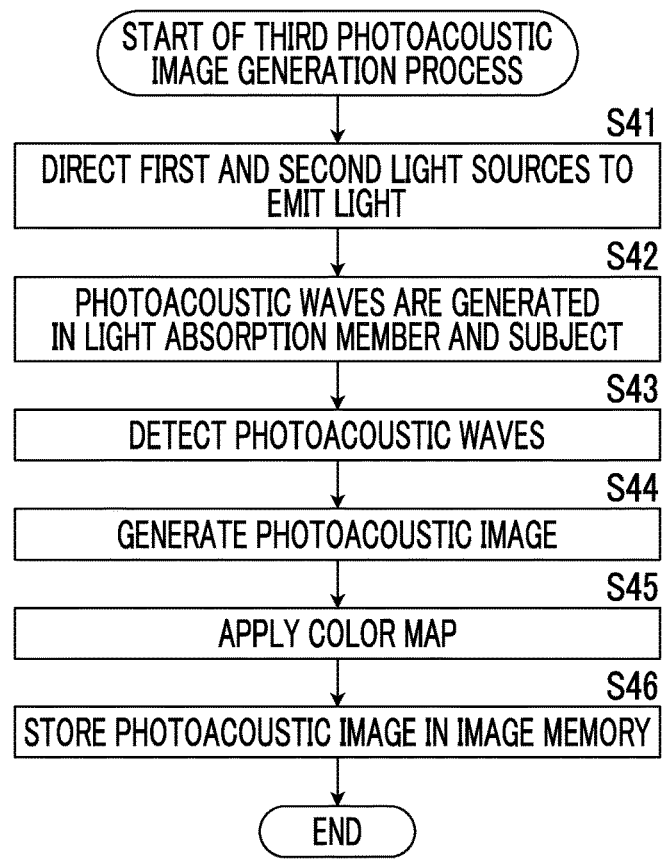
FIG. 8 is a flowchart illustrating the procedure of a third photoacoustic image generation process.

FIG. 8 illustrates the procedure of the third photoacoustic image generation process. The control means 28 directs the first light source 13 and the second light source 14 to emit light (Step S41). The emission of light from the first light source 13 by the control means 28 is performed in the same procedure as that in Step S21 of FIG. 6. The emission of light from the second light source 14 is performed in the same procedure as that in Step S31 of FIG. 7.

The pulsed laser light emitted from the first light source 13 is incident on the optical fiber 153 through the optical fiber 17 and the optical connector 19, is guided to the vicinity of the leading end of the puncture needle 15 by the optical fiber 153, and is emitted from the first light emitting portion 153a (see FIG. 2). At least a portion of the pulsed laser light is emitted to the light absorption member 51 provided at the leading end of the puncture needle 15. In addition, the pulsed laser light emitted from the second light source 14 is incident on the optical fiber 154 through the optical fiber 18 and the optical connector 20, is guided to the vicinity of the leading end of the puncture needle 15 by the optical fiber 154, is emitted from the second light emitting portion 154a (see FIG. 2), passes through the light absorption member 51, and is emitted into the subject through the opening of the puncture needle 15. The light absorption member 51 absorbs the light with the first wavelength and generates photoacoustic waves (first photoacoustic waves). The absorber that is present in the emission range of the pulsed laser light with the second wavelength absorbs light with the second wavelength and generates photoacoustic waves (second photoacoustic waves) (Step S42).

The probe 11 detects the photoacoustic waves generated by the emission of the laser light, that is, the first photoacoustic waves generated from the light absorption member 51 and the second photoacoustic waves generated from the absorber in the subject (Step S43). The photoacoustic waves detected by the probe are received by the receiving circuit 21 and the sampling data of the photoacoustic waves is stored in the receiving memory 22. The photoacoustic image generation means 24 receives the sampling data of the detection signal of the photoacoustic waves through the data demultiplexing means 23 and generates a photoacoustic image (third photoacoustic image) (Step S44). The photoacoustic image generation means 24 may apply a color map (Step S45) to convert the signal intensity of the photoacoustic image into a color. The photoacoustic image generated by the photoacoustic image generation means 24 is stored in, for example, the image memory (not illustrated) of the image output means 26 (Step S46).

Figure 9:
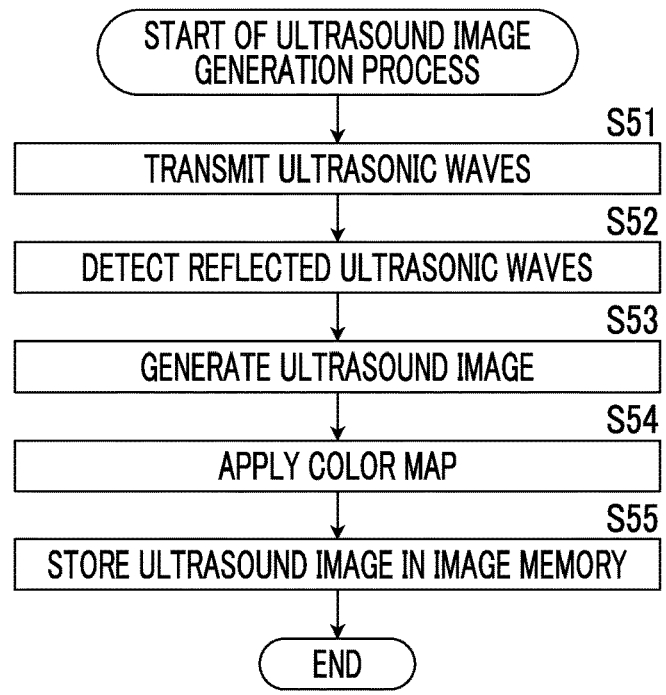
FIG. 9 is a flowchart illustrating the procedure of an ultrasound image generation process.

FIG. 9 illustrates the procedure of the ultrasound image generation process. The control means 28 transmits an ultrasound trigger signal to the transmission control circuit 27. The transmission control circuit 27 directs the probe 11 to transmit ultrasonic waves in response to the ultrasound trigger signal (Step S51). The probe 11 transmits ultrasonic waves and detects reflected ultrasonic waves (Step S52). The reflected ultrasonic waves detected by the probe 11 are received by the receiving circuit 21 and the sampling data of the reflected ultrasonic waves is stored in the receiving memory 22. The ultrasound image generation means 25 receives the sampling data of the detection signal of the reflected ultrasonic waves through the data demultiplexing means 23 and generates an ultrasound image (Step S53). The ultrasound image generation means 25 may apply a color map (Step S54) to convert the signal intensity of the ultrasound image into a color. The ultrasound image generated by the ultrasound image generation means 25 is stored in, for example, the image memory (not illustrated) of the image output means 26 (Step S55).

The user can appropriately switch the operation mode among the first to fourth operation modes while inserting the puncture needle 15. For example, when starting the insertion of the puncture needle 15, the user selects the fourth operation mode and performs an operation such that an ultrasound image is displayed on the image display means 16. After starting the insertion, the user switches the operation mode to the first operation mode and performs an operation such that the first photoacoustic image is displayed on the image display means 16. In the first photoacoustic image, the position of the light absorption member 51 that absorbs light with the first wavelength and generates photoacoustic waves appears as a bright point. Therefore, it is possible to check the position of the leading end of the puncture needle 15 with reference to the first photoacoustic image.

In a case in which the puncture needle 15 is inserted to a certain depth, the user switches the operation mode to the second operation mode and performs an operation such that the second photoacoustic image is displayed on the image display means 16. In a case in which a light absorber that absorbs light with the second wavelength is present in the vicinity of the leading end of the puncture needle 15 in the subject, the position of the light absorber appears as a bright point in the second photoacoustic image. For example, in a case in which the second wavelength is a wavelength absorbed by blood and blood is present in the vicinity of the leading end of the puncture needle 15, a bright point appears in the second photoacoustic image. The user can determine whether the puncture needle 15 has been inserted to the part in which blood is present, on the basis of whether a bright point is present. The photoacoustic image generation apparatus 10 may determine whether the sum of the signals of the second photoacoustic image is equal to or greater than a threshold value. In a case in which the sum of the signals is equal to or greater than the threshold value, the photoacoustic image generation apparatus 10 may notify the user of the determination result. The user may perform a needling operation while alternately switching the operation mode between the first operation mode and the second operation mode or after selecting the third operation mode.

In the above description, the first photoacoustic image, the second photoacoustic image, the third photoacoustic image, and the ultrasound image are generated in the independent operation modes. However, the invention is not limited thereto. For example, at least one of the first photoacoustic image, the second photoacoustic image, or the third photoacoustic image and the ultrasound image may be generated in one operation mode. In this case, the image output means 26 may function as image combination means for combining at least two of the first photoacoustic image, the second photoacoustic image, the third photoacoustic image, and the ultrasound image. For example, the image output means 26 may combine the first photoacoustic image and the ultrasound image and display a composite image on the image display means 16. Alternatively, the image output means 26 may combine the second photoacoustic image and the ultrasound image and display a composite image on the image display means 16. The image output means 26 may combine the third photoacoustic image and the ultrasound image and display a composite image on the image display means 16. In addition, the image output means 26 may combine the first photoacoustic image, the second photoacoustic image, and the ultrasound image and display a composite image on the image display means 16.

In this embodiment, the light with the first wavelength emitted from the first light source 13 is emitted to the light absorption member 51 through the optical fiber 17 and the optical fiber 153 and the light with the second wavelength emitted from the second light source 14 is emitted to the light absorption member 51 through the optical fiber 18 and the optical fiber 154. In a case in which the light absorption member 51 is irradiated with the light with the first wavelength, the light absorption member 51 generates photoacoustic waves and the first photoacoustic image is generated on the basis of the detection signal of the photoacoustic waves. The first photoacoustic image includes the positional information of the leading end of the puncture needle 15. In contrast, in a case in which the light absorption member 51 is irradiated with the light with the second wavelength, the light absorption member 51 transmits the light with the second wavelength and the light with the second wavelength is emitted from the leading end of the puncture needle 15 to the subject. In a case in which a light absorber is present in the part irradiated with the light with the second wavelength in the subject, photoacoustic waves are generated from the light absorber and the second photoacoustic image is generated on the basis of the detection signal of the photoacoustic waves. The second photoacoustic image includes surrounding environment information.

In this embodiment, the light absorption member 51 that absorbs light with the first wavelength, generates photoacoustic waves, and transmits light with the second wavelength without absorbing the light with the second wavelength is used. As such, the light absorption member 51 is used and is selectively irradiated with the light with the first wavelength and the light with the second wavelength. Therefore, it is possible to separately acquire both the positional information and the surrounding environment information of the tip of the needle, using one puncture needle 15. In a case in which a wavelength that is absorbed by a material in the part to be needled to generate photoacoustic waves is selected as the second wavelength, it is possible to determine whether the puncture needle 15 has been inserted into the part to be needled, using the second photoacoustic image. In this embodiment, in the puncture needle 15, the optical fiber 153 is used to guide light with the first wavelength and the optical fiber 154 is used to guide light with the second wavelength. Since the light with the first wavelength and the light with the second wavelength are guided by the individual optical fibers, it is possible to irradiate the light absorption member 51 with the light with the first wavelength and the light with the second wavelength at the same time. In this case, it is possible to acquire the positional information and the surrounding environment information of the tip of the needle at the same time.

Here, in JP2013-13713A, it is difficult to separate the photoacoustic waves generated by the absorption of light emitted from the light emitting unit by a light absorber which is present in front of the needle in the needling direction in the subject from the photoacoustic waves generated by the absorption of light emitted from the light emitting unit by, for example, metal forming the puncture needle main body. Therefore, two bright points are mixed in the photoacoustic image. In some cases, since the intensity of the detected photoacoustic waves is sequentially changed by the movement of the body or the movement of the probe, a bright point blinks in the photoacoustic image. In JP2013-13713A, in a case in which a reduction in the brightness of the bright point occurs in the photoacoustic image, the operator needs to perform, for example, an operation of changing the position or angle of the ultrasound probe to reconfirm the position or angle of the probe at which the brightness is the maximum. That is, JP2013-13713A has the problem that the operator needs to perform an unnecessary operation. However, in this embodiment, in a case in which light is not emitted from the first light source 13 and the second light source 14 at the same time, the positional information and the surrounding environment information are separated from each other. Therefore, the above-mentioned problems do not occur. In addition, in this embodiment, in a case in which light with the first wavelength and light with the second wavelength are emitted to the light absorption member 51 to acquire the positional information and the surrounding environment information of the tip of the needle at the same time, the positional information of the tip of the needle is acquired on the basis of the photoacoustic waves generated from the light absorption member 51. Therefore, the positional information of the tip of the needle can be more clearly acquired than that in JP2013-13713A in which the light absorption member 51 is not provided.

Next, a second embodiment of the invention will be described. This embodiment differs from the first embodiment in that the puncture needle 15 further includes a phosphor. The phosphor is provided at the position that is irradiated with light emitted from the second light emitting portion 154a (see FIG. 2) and converts light with the second wavelength emitted from the second light emitting portion 154a into light with a third wavelength. The third wavelength is different from the first wavelength and the second wavelength. In this embodiment, in a case in which the second light source 14 emits light with the second wavelength, the subject is not irradiated with the light with the second wavelength, but is irradiated with the light with the third wavelength. The other configurations may be the same as those in the first embodiment.

It is preferable that the phosphor emits light, for example, in a nanosecond order. For example, a quantum dot or an organic phosphor (organic pigment) is used as the phosphor. It is preferable that the quantum dot is a PbS-based quantum dot. For example, a quantum dot manufactured by Evident Technologies Inc. is used. The phosphor is mixed with, for example, the light absorption member 51. Specifically, a light absorber that absorbs light with the first wavelength and transmits light with the second wavelength and the phosphor are mixed with a resin such as an epoxy resin. Alternatively, the first light emitting portion 153a and the second light emitting portion 154a may be covered with the resin having the phosphor mixed therewith and each resin having the phosphor mixed therewith may be covered with the resin having the light absorber mixed therewith. On the contrary, the first light emitting portion 153a and the second light emitting portion 154a may be covered with the resin having the light absorber mixed therewith and then may be covered with the resin having the phosphor mixed therewith.

The phosphor mixed with the light absorption member 51 varies depending on the puncture needle 15. For example, in a case in which there are a plurality of puncture needles 15, the wavelength of light emitted from the second light source 14 may be maintained to be the second wavelength and the wavelength of fluorescent light emitted from the phosphor may vary depending on the puncture needles 15. For example, the puncture needle 15 for blood includes a phosphor that converts light with the second wavelength into light with a wavelength of 530 nm. In contrast, the puncture needle 15 for a nerve includes a phosphor that converts light with the second wavelength into light with a wavelength of 1210 nm. In a case in which the part to be needled is a blood vessel, the puncture needle 15 for blood is used. In a case in which the part to be needled is a nerve, the puncture needle for a nerve is used. In this way, it is possible to select the target of which the surrounding environment information is to be evaluated, without changing the wavelength of light emitted from the second light source 14.

Figure 10:
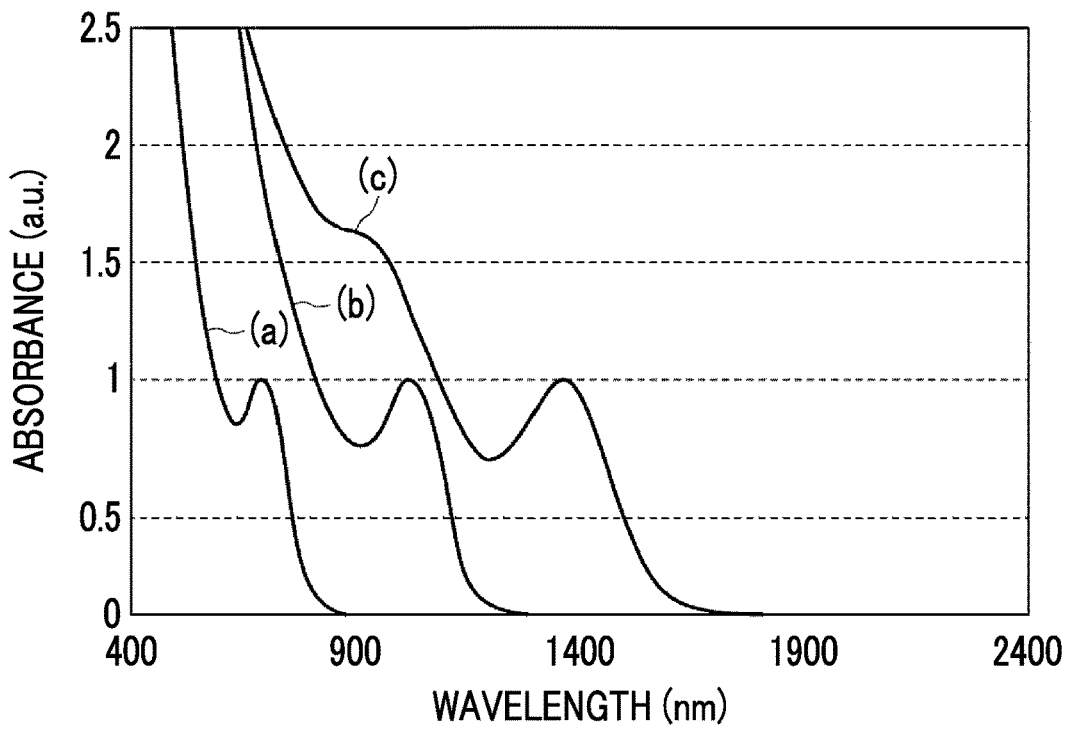
FIG. 10 is a graph illustrating the absorbance-wavelength characteristics of a phosphor.

FIG. 10 illustrates the absorbance-wavelength characteristics of the phosphor. The horizontal axis indicates a wavelength and the vertical axis indicates absorbance. FIG. 10 illustrates the absorbance-wavelength characteristics of three PbS-based phosphors (quantum dots) represented by graphs (a) to (c). As can be seen from FIG. 10, these phosphors have high absorbance in the wavelength range of about 400 nm to 500 nm. Therefore, it is preferable that a light source which emits light with a wavelength of 400 nm to 500 nm is used as the second light source 14. In a case in which the first wavelength is 905 nm, the phosphors represented by the graphs (b) and (c) absorb a certain amount of light and generate photoacoustic waves. However, the intensity of the generated photoacoustic waves is sufficiently lower than that of the photoacoustic waves generated from the light absorber of the light absorption member 51 and is as low as the level of noise, which causes no problem.

Figure 11:
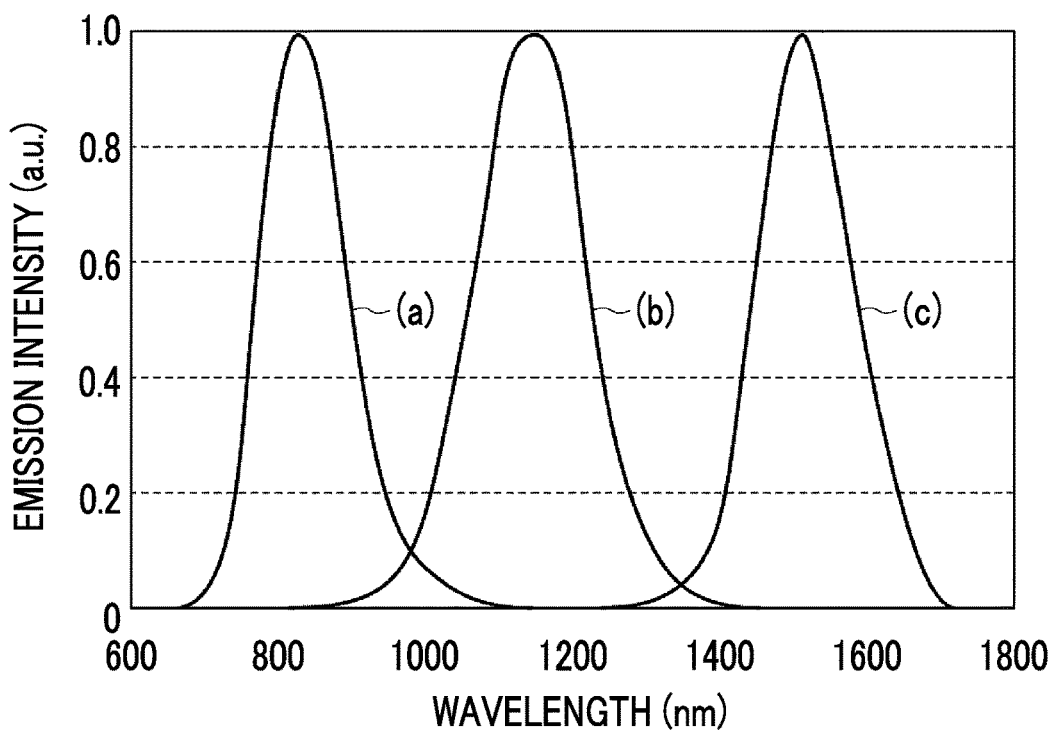
FIG. 11 is a graph illustrating the emission intensity-wavelength characteristics of the phosphor.

FIG. 11 illustrates the fluorescent emission intensity-wavelength characteristics of the phosphor. The horizontal axis indicates a wavelength and the vertical axis indicates emission intensity. FIG. 11 illustrates the emission intensity-wavelength characteristics of three PbS-based phosphors (quantum dots) represented by graphs (a) to (c). The phosphor represented by the graph (a) generates fluorescent light with a wavelength of about 800 nm, using light with the second wavelength as excitation light. The phosphor represented by the graph (b) generates fluorescent light with a wavelength of about 1100 nm, using light with the second wavelength as excitation light. The phosphor represented by the graph (c) generates fluorescent light with a wavelength of about 1500 nm, using light with the second wavelength as excitation light. As such, it is possible to generate fluorescent light components with different wavelengths according to the phosphor used, while maintaining the second wavelength.

In this embodiment, the puncture needle 15 includes the phosphor that converts light with the second wavelength into light with the third wavelength. In this case, the photoacoustic waves generated by the emission of the light with the third wavelength are detected and the second photoacoustic image is generated on the basis of the detection signal of the photoacoustic waves. In this way, it is possible to evaluate the surrounding environment of the leading end of the puncture needle 15. In this embodiment, the phosphor used is changed to change the wavelength of fluorescent light. Therefore, even in a case in which there are a plurality of evaluation targets, it is not necessary to prepare light sources that emit light components with a plurality of wavelengths. As a result, it is possible to prevent an increase in the overall cost of the apparatus. The other effects are the same as those in the first embodiment.

Next, a third embodiment of the invention will be described. This embodiment differs from the first and second embodiments in that the puncture needle 15 includes an outer needle and an inner needle. The other configurations may be the same as those in the first embodiment or the second embodiment.

Figure 12:
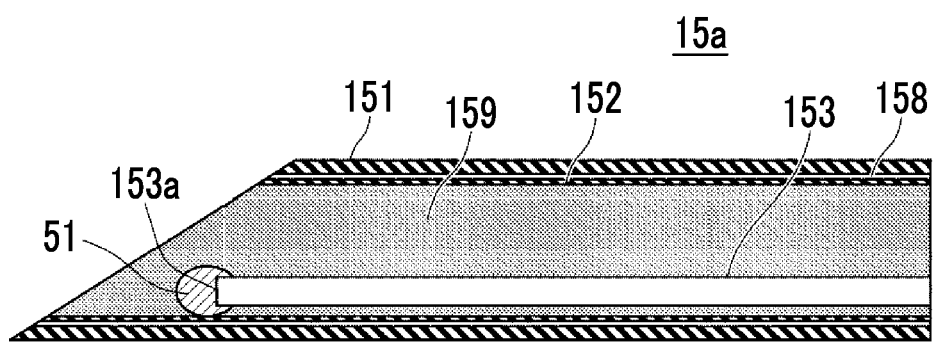
FIG. 12 is a cross-sectional view illustrating the vicinity of a leading end of a puncture needle according to a third embodiment of the invention.

FIG. 12 is a cross-sectional view illustrating a puncture needle 15a according to this embodiment. In FIG. 12, the optical fiber 154 (see FIG. 2) is not illustrated. A puncture needle main body 151 forming the outer needle has an opening at an acute leading end and has an inner cavity. An inner needle 152 has substantially the same outside diameter as the inner cavity of the puncture needle main body 151 and is configured so as to be inserted into or removed from the hollow puncture needle main body 151. The inner needle 152 is inserted into the inner cavity of the puncture needle main body 151 from the base end side of the puncture needle main body 151 to seal at least a portion of the inner cavity of the puncture needle main body 151 to the extent that, for example, a section of the living body is prevented from being inserted into the inner cavity. A protruding portion for connection position adjustment is provided in a base end portion of the inner needle 152. A groove into which the protruding portion provided in the base end portion of the inner needle 152 is fitted is provided in a base end portion of the puncture needle main body 151. In a case in which the inner needle 152 is set in the puncture needle main body 151, the protrusion portion provided in the base end portion of the inner needle 152 and the groove provided in the base end portion of the puncture needle main body 151 are positioned and the base end portion of the inner needle 152 is fitted to the base end portion of the puncture needle main body 151.

The inner needle 152 includes the optical fiber 153, the optical fiber 154 (not illustrated in FIG. 12), the light absorption member 51, a tube 158, and a transparent resin 159. The tube 158 is, for example, a hollow tube made of polyimide. The tube 158 may be a metal tube made of, for example, stainless steel. The outside diameter of the tube 158 is slightly less than the diameter of the inner cavity of the puncture needle main body 151. The transparent resin 159 is provided in the tube 158. For example, an epoxy resin (adhesive) is used as the transparent resin 159. The tube 158 and the transparent resin 159 are acute, similarly to the acute leading end of the puncture needle. A photocurable resin, a thermosetting resin, or a room-temperature-curable resin may be used as the transparent resin 159.

The optical fiber 153 and the optical fiber 154 are covered with the transparent resin 159 in the tube 158. The light absorption member 51 is provided at the leading ends of the optical fiber 153 and the optical fiber 154. The light absorption member 51 is irradiated with light emitted from the first light emitting portion 153a and the second light emitting portion 154a. The light absorption member 51 may further include the phosphor described in the second embodiment. In a case in which the first light source 13 (see FIG. 1) emits light, the light absorption member 51 absorbs the emitted light with the first wavelength and photoacoustic waves are generated at the leading end of the puncture needle.

An operator, such as a doctor, inserts the puncture needle 15a into the subject, with the inner needle 152 set in the puncture needle main body 151. Since the inner cavity of the puncture needle main body 151 is closed by the inner needle 152, it is possible to prevent a piece of flesh from getting into the needle while the needle is being inserted and thus to prevent the needling sense of the operator from being hindered. In addition, it is possible to prevent the inflow of water from the part to be needled to the inner cavity of the puncture needle main body 151. After inserting the needle into the subject, the operator releases the connection between the base end portion of the inner needle 152 and the base end portion of the puncture needle main body 151 and takes the inner needle 152 out of the puncture needle main body 151. After taking the inner needle 152 out of the puncture needle main body 151, the operator can attach, for example, a syringe to the base end portion of the puncture needle main body 151 and inject a medicine such as an anesthetic.

Figure 13:
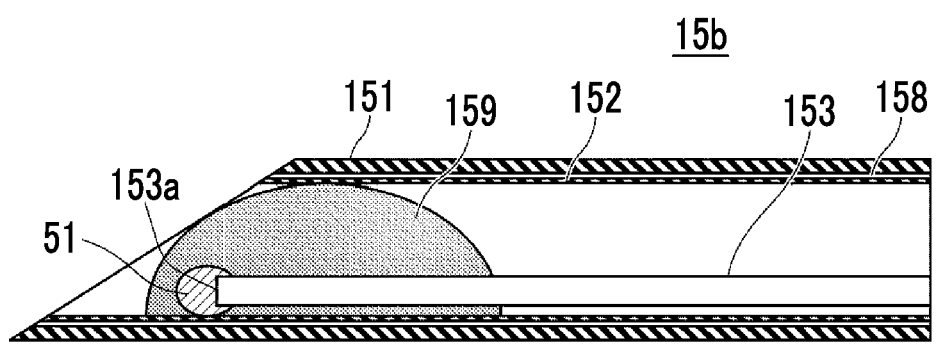
FIG. 13 is a cross-sectional view illustrating the vicinity of a leading end of a puncture needle according to a modification example.

In addition, the transparent resin 159 may close at least a leading end portion of the tube 158 and does not necessarily close the entire inside of the tube 158. FIG. 13 is a cross-sectional view illustrating the vicinity of the leading end of a puncture needle according to a modification example. In a puncture needle 15b, a transparent resin 159 covers the light absorption member 51 covering the light emitting portion 153a of the optical fiber 153 and the light emitting portion 154a of the optical fiber 154 (not illustrated in FIG. 13) and (the leading end portions of) the optical fibers 153 and 154 and the light absorption member 51 are fixed to the inner wall of the tube 158 by the transparent resin 159. In addition, the transparent resin 159 closes an opening provided in the leading end portion of the tube 158. In a case in which this configuration is used, it is also possible to prevent the inflow of, for example, water into the inner needle 152.

The optical fiber 153 and the optical fiber 154 do not need to be fixed to the inner wall of the tube 158 by the transparent resin 159 and may be fixed to the inner cavity of the tube 158 by the light absorption member 51. The leading end portion of the tube 158 may be closed by the light absorption member 51. In this case, the transparent resin 159 may be omitted. In addition, instead of the configuration in which the optical fiber 153 and the optical fiber 154 are covered with the transparent resin 159, the optical fiber 153 and the optical fiber 154 may be covered with a resin with which at least one of the light absorber described in the first embodiment or the phosphor described in the second embodiment is mixed.

In this embodiment, the puncture needle 15b includes the inner needle 152 provided in the inner cavity of the puncture needle main body 151. The inner needle 152 closes the inner cavity of the puncture needle main body 151 while the puncture needle 15b is being inserted. Therefore, it is possible to prevent the needling sense of the operator from being hindered and to prevent the inflow of water from the part to be needled to the inner cavity of the puncture needle main body 151. The other effects are the same as those in the first embodiment or the second embodiment.

In the above-described embodiments, the puncture needle 15 is considered as an insert. However, the invention is not limited thereto. The insert may be a radio frequency ablation needle including an electrode that is used for radio frequency ablation, a catheter that is inserted into a blood vessel, or a guide wire for a catheter that is inserted into a blood vessel. Alternatively, the insert may be an optical fiber for laser treatment.

In the above-described embodiments, a needle having an opening at the leading end is assumed as the needle. However, the opening is not necessarily provided at the leading end of the needle. The needle is not limited to an injection needle and may be a biopsy needle used for biopsy. That is, the needle may be a biopsy needle that is inserted into an inspection target of the living body and extracts the tissues of a biopsy site of the inspection target. In this case, photoacoustic waves may be generated from an extraction portion (intake port) for sucking and extracting the tissues of the biopsy site. In addition, the needle may be used as a guiding needle that is used for insertion into a deep part, such as a part under the skin or an organ inside the abdomen.

The puncture needle 15 is not limited to the needle that is inserted from the outside of the subject into the subject through the skin and may be a needle for ultrasound endoscopy. The optical fibers 153 and 154 and the light absorption member 51 may be provided in the needle for ultrasound endoscopy. The light absorption member 51 provided in the leading end portion of the needle may be irradiated with at least one of light with the first wavelength or light with the second wavelength. Then, photoacoustic waves may be detected and a photoacoustic image (the first photoacoustic image, the second photoacoustic image, or the third photoacoustic image) may be generated. In this case, it is possible to perform needling while observing the first photoacoustic image and checking the position of the leading end portion of the needle for ultrasound endoscopy. In addition, it is possible to determine whether an evaluation target material is present in the vicinity of the needle, using the second photoacoustic image. In a case in which the third photoacoustic image is generated, it is possible to determine the position of the tip of the needle and to determine whether an evaluation target material is present. The first photoacoustic waves generated from the leading end portion of the needle for ultrasound endoscopy and the second photoacoustic waves generated from the vicinity of the leading end portion may be detected by a probe for body surface or a probe that is incorporated into an endoscope.

Figure 14:
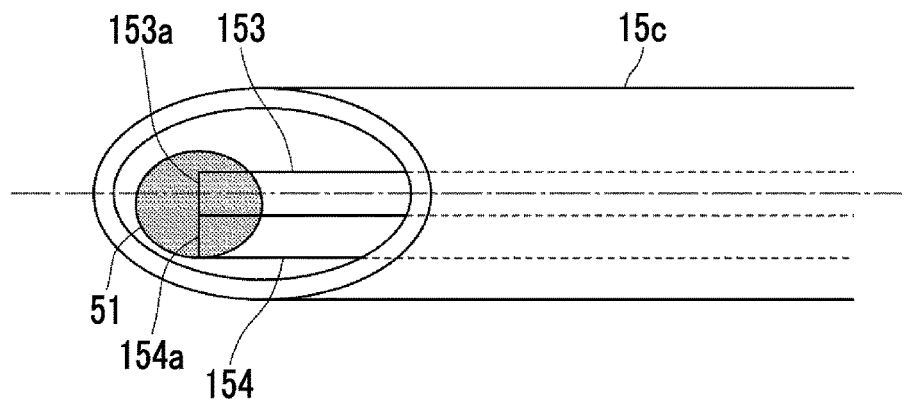
FIG. 14 is a top view illustrating a puncture needle according to another modification example.

The optical fiber 153 and the optical fiber 154 in the puncture needle 15 have any positional relationship therebetween. FIG. 14 illustrates a puncture needle according to another modification example. In this modification example, similarly to the puncture needle illustrated in FIG. 2, the optical fiber 153 and the optical fiber 154 are disposed so as to be adjacent to each other in the puncture needle 15c. In FIG. 14, particularly, of two optical fibers, the optical fiber 153 that guides light with the first wavelength is disposed at the center of a puncture needle 15c in a width direction. Here, the position of the center of the puncture needle in the width direction means the position of the center in the width direction in a case in which the needle is viewed from the upper side with a sharp portion of the leading end of the needle facing down or up. As illustrated in FIG. 14, in a case in which the first light emitting portion 153a provided at the leading end of the optical fiber 153 is disposed at the center of (the opening of) the puncture needle 15 in the width direction, it is possible to generate the first photoacoustic waves at the center of the puncture needle 15c in the width direction.

Figure 15:
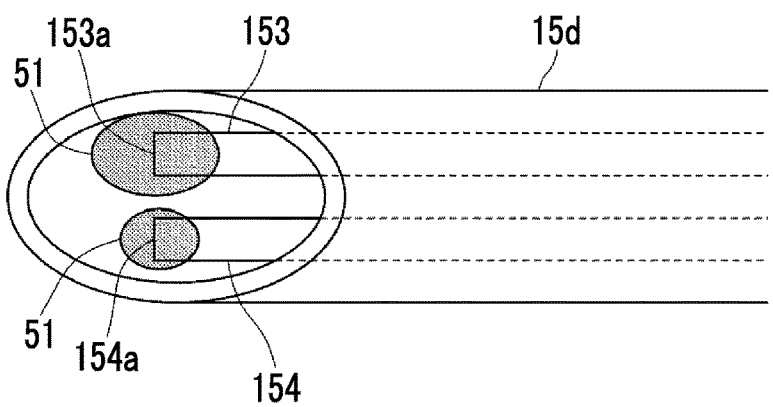
FIG. 15 is a top view illustrating a puncture needle according to still another modification example.

The optical fiber 153 and the optical fiber 154 are not necessarily disposed so as to be adjacent to each other. FIG. 15 illustrates a puncture needle according to still another modification example. In a puncture needle 15d according to this modification example, the optical fiber 153 and the optical fiber 154 are disposed with a gap therebetween. In this case, instead of the configuration in which one light absorption member 51 covers the first light emitting portion 153a and the second light emitting portion 154a, the first light emitting portion 153a and the second light emitting portion 154a may be separately covered with the light absorption member 51, as illustrated in FIG. 15. In this case, it is preferable that the amount of light absorption member 51 covering the first light emitting portion 153a is more than the amount of light absorption member 51 covering the second light emitting portion 154a in order to generate the first photoacoustic waves with sufficiently high intensity. The second light emitting portion 154a may be covered with a transparent resin instead of the light absorption member 51.

Figure 16:
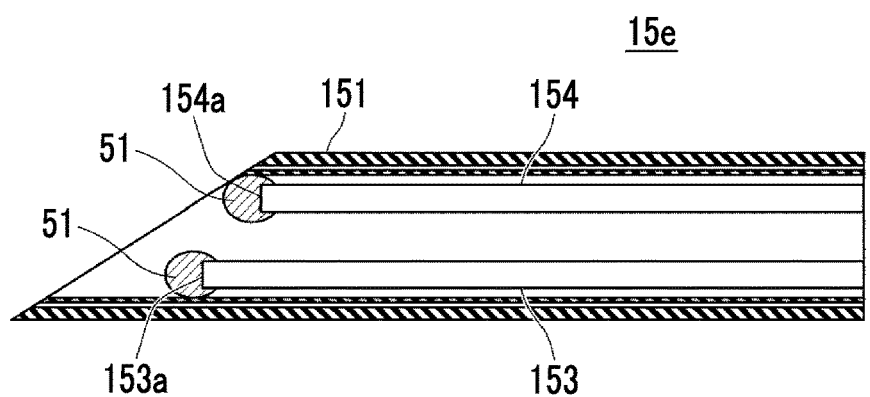
FIG. 16 is a cross-sectional view illustrating a puncture needle according to yet another modification example.

The optical fiber 153 and the optical fiber 154 are not necessarily arranged in the width direction of the puncture needle. FIG. 16 illustrates a puncture needle according to yet another modification example. In a puncture needle 15e according to this modification example, the optical fiber 153 is provided on an inner wall on the side where the puncture needle main body 151 is the longest and the leading end is sharp. In contrast, the optical fiber 154 is provided on an inner wall (a position that is rotated 180° about the axial direction of the puncture needle) opposite to the inner wall. In this modification example, the first light emitting portion 153a provided at the leading end of the optical fiber 153 and the second light emitting portion 154a provided at the leading end of the optical fiber 154 are separated from each other. In this modification example, the second light emitting portion 154a may be covered with a transparent resin as described in the modification example illustrated in FIG. 15.

The invention has been described above on the basis of the preferred embodiments. However, the photoacoustic image generation apparatus and the insert according to the invention are not limited to the above-described embodiments. Various modifications and changes of the configurations according to the above-described embodiments are also included in the scope of the invention.

In the above description, it is preferable that an amount of light absorption member covering the first light emitting portion is more than an amount of light absorption member covering the second light emitting portion.

The light absorption member may include a light absorber that absorbs the light with the first wavelength and transmits the light with the second wavelength and a resin including the light absorber.

The insert according to the invention may have an inner cavity. The light absorption member may function as a fixing member that fixes the light guide members to an inner wall of the inner cavity of the insert.

The insert according to the invention may further includes a transparent resin that transmits at least the light with the second wavelength. In this case, the light absorption member may be covered with the transparent resin.

The insert according to the invention may have an inner cavity. The first light guide member, the second light guide member, and the light absorption member may be fixed to an inner wall of the inner cavity of the insert by the transparent resin.

The insert according to the invention may be a puncture needle having an inner cavity. In this case, the puncture needle may further include a hollow tube in which the first light guide member and the second light guide member are accommodated.

In the invention, the puncture needle may include an inner needle and an outer needle. In this case, the inner needle may include the hollow tube. The inner needle may seal at least a portion of the inner cavity.

In the invention, the light absorption member may function as a fixing member that fixes the light guide members to an inner wall of the hollow tube.

The insert according to the invention may further include a transparent resin that transmits at least the light with the second wavelength. The first light guide member, the second light guide member, and the light absorption member may be fixed to an inner wall of the hollow tube by the transparent resin.

In the invention, it is preferable that the first light emitting portion is provided at a center of the insert in a width direction.

The insert according to the invention may further include a phosphor that converts the light with the second wavelength emitted from the second light emitting portion into light with a third wavelength different from the first wavelength and the second wavelength.

Preferably, the insert according to the invention further includes: an optical connector that detachably connects the first light guide member and an optical fiber which guides the light with the first wavelength emitted from a first light source; and an optical connector that detachably connects the second light guide member and an optical fiber which guides the light with the second wavelength emitted from a second light source.

In the above description, the second photoacoustic waves may be generated by the absorption of the light with the second wavelength transmitted through the light absorption member by the subject.

The insert may further include a phosphor that converts the light with the second wavelength emitted from the second light emitting portion into light with a third wavelength different from the first wavelength and the second wavelength. In this case, the second photoacoustic waves may be generated by the absorption of the light with the third wavelength emitted from the phosphor by the subject.

In the photoacoustic image generation apparatus according to the invention, the acoustic wave detection unit may further detect reflected acoustic waves with respect to acoustic waves transmitted to the subject. In this case, preferably, the photoacoustic image generation apparatus further includes reflected acoustic image generation unit for generating a reflected acoustic image on the basis of the reflected acoustic waves.

The photoacoustic image generation apparatus according to the invention may further include image combination unit for combining at least one of the first photoacoustic image, the second photoacoustic image, or the third photoacoustic image and the reflected acoustic image.

The photoacoustic image generation apparatus and the insert according to the invention can acquire both the positional information and the surrounding environment information of the insert.

What is claimed is:

1. An insert that is at least partially inserted into a subject, comprising:
    a first light guide member that guides light with a first wavelength;
    a first light emitting portion from which the light guided by the first light guide member is emitted;
    a second light guide member that guides light with a second wavelength different from the first wavelength;
    a second light emitting portion from which the light guided by the second light guide member is emitted; and
    a light absorption member that at least partially covers both the first light emitting portion and the second light emitting portion, absorbs the light with the first wavelength emitted from the first light emitting portion to generate photoacoustic waves, and transmits the light with the second wavelength emitted from the second light emitting portion,
    wherein an amount of light absorption member covering the first light emitting portion is more than an amount of light absorption member covering the second light emitting portion.

2. The insert according to claim 1,
    wherein the light absorption member includes a light absorber that absorbs the light with the first wavelength and transmits the light with the second wavelength and a resin including the light absorber.

3. The insert according to claim 1,
    wherein the insert has an inner cavity, and
    the light absorption member functions as a fixing member that fixes the first light guide member and the second light guide member to an inner wall of the inner cavity.

4. The insert according to claim 1, further comprising:
    a transparent resin that transmits at least the light with the second wavelength,
    wherein the light absorption member is covered with the transparent resin.

5. The insert according to claim 4,
    wherein the insert has an inner cavity, and
    the first light guide member, the second light guide member, and the light absorption member are fixed to an inner wall of the inner cavity by the transparent resin.

6. The insert according to claim 1,
    wherein the insert is a puncture needle having an inner cavity, and the insert further includes a hollow tube in which the first light guide member and the second light guide member are accommodated.

7. The insert according to claim 6,
wherein the puncture needle includes an inner needle and an outer needle,
the inner needle includes the hollow tube, and
the inner needle seals at least a portion of the inner cavity.

8. The insert according to claim 6,
wherein the light absorption member functions as a fixing member that fixes the first light guide member and the second light guide member to an inner wall of the hollow tube.

9. The insert according to claim 6, further comprising:
a transparent resin that transmits at least the light with the second wavelength,
wherein the first light guide member, the second light guide member, and the light absorption member are fixed to an inner wall of the hollow tube by the transparent resin.

10. The insert according to claim 1,
wherein the first light emitting portion is provided at a center of the insert in a width direction.

11. The insert according to claim 1, further comprising:
an optical connector that detachably connects the first light guide member and an optical fiber which guides the light with the first wavelength emitted from a first light source; and
an optical connector that detachably connects the second light guide member and an optical fiber which guides the light with the second wavelength emitted from a second light source.

12. An insert that is at least partially inserted into a subject, comprising:
a first light guide member that guides light with a first wavelength;
a first light emitting portion from which the light guided by the first light guide member is emitted;
a second light guide member that guides light with a second wavelength different from the first wavelength;
a second light emitting portion from which the light guided by the second light guide member is emitted;
a light absorption member that at least partially covers both the first light emitting portion and the second light emitting portion, absorbs the light with the first wavelength emitted from the first light emitting portion to generate photoacoustic waves, and transmits the light with the second wavelength emitted from the second light emitting portion; and
a phosphor that converts the light with the second wavelength emitted from the second light emitting portion into light with a third wavelength different from the first wavelength and the second wavelength.

13. The insert according to claim 12,
wherein the light absorption member includes a light absorber that absorbs the light with the first wavelength and transmits the light with the second wavelength and a resin including the light absorber.

14. The insert according to claim 12,
wherein the insert has an inner cavity, and
the light absorption member functions as a fixing member that fixes the first light guide member and the second light guide member to an inner wall of the inner cavity.

15. The insert according to claim 12, further comprising:
a transparent resin that transmits at least the light with the second wavelength,
wherein the light absorption member is covered with the transparent resin.

16. The insert according to claim 12,
wherein the insert has an inner cavity, and
the first light guide member, the second light guide member, and the light absorption member are fixed to an inner wall of the inner cavity by the transparent resin.

17. The insert according to claim 12,
wherein the insert is a puncture needle having an inner cavity, and
the insert further includes a hollow tube in which the first light guide member and the second light guide member are accommodated.

18. The insert according to claim 12,
wherein the puncture needle includes an inner needle and an outer needle,
the inner needle includes the hollow tube, and
the inner needle seals at least a portion of the inner cavity.

19. The insert according to claim 12,
wherein the light absorption member functions as a fixing member that fixes the first light guide member and the second light guide member to an inner wall of the hollow tube.

20. The insert according to claim 12, further comprising:
a transparent resin that transmits at least the light with the second wavelength,
wherein the first light guide member, the second light guide member, and the light absorption member are fixed to an inner wall of the hollow tube by the transparent resin.

21. The insert according to claim 12,
wherein the first light emitting portion is provided at a center of the insert in a width direction.

22. The insert according to claim 12, further comprising:
an optical connector that detachably connects the first light guide member and an optical fiber which guides the light with the first wavelength emitted from a first light source; and
an optical connector that detachably connects the second light guide member and an optical fiber which guides the light with the second wavelength emitted from a second light source.

23. A photoacoustic image generation apparatus comprising:
a first light source that emits light with a first wavelength;
a second light source that emits light with a second wavelength different from the first wavelength;
an insert that is at least partially inserted into a subject and comprises a first light guide member which guides the light with the first wavelength, a first light emitting portion from which the light guided by the first light guide member is emitted, a second light guide member which guides the light with the second wavelength, a second light emitting portion from which the light guided by the second light guide member is emitted, and a light absorption member which at least partially covers both the first light emitting portion and the second light emitting portion, absorbs the light with the first wavelength emitted from the first light emitting portion to generate photoacoustic waves, and transmits the light with the second wavelength emitted from the second light emitting portion;
a probe configured to detect first photoacoustic waves which are generated by the absorption of the light with the first wavelength by the light absorption member and second photoacoustic waves which are generated in the subject due to the light emitted from the second light emitting portion; and a processor configured to generate a first photoacoustic image on the basis of the first photoacoustic waves and a second photoacoustic image on the basis of the second photoacoustic waves.

24. The photoacoustic image generation apparatus according to claim 23, wherein the second photoacoustic waves are generated by the absorption of the light with the second wavelength transmitted through the light absorption member by the subject.

25. The photoacoustic image generation apparatus according to claim 23, wherein the insert further includes a phosphor that converts the light with the second wavelength emitted from the second light emitting portion into light with a third wavelength different from the first wavelength and the second wavelength, and the second photoacoustic waves are generated by the absorption of the light with the third wavelength emitted from the phosphor by the subject.

26. The photoacoustic image generation apparatus according to claim 23, wherein the probe is further configured to detect reflected acoustic waves with respect to acoustic waves transmitted to the subject, and the processor is further configured to generate a reflected acoustic image on the basis of the reflected acoustic waves.

27. The photoacoustic image generation apparatus according to claim 26, wherein the processor is further configured to combine at least one of the first photoacoustic image or the second photoacoustic image, and the reflected acoustic image.

28. The photoacoustic image generation apparatus according to claim 23, wherein the processor is further configured to generate a third photoacoustic image on the basis of both the first photoacoustic waves and the second photoacoustic waves.

* * * * *